United States Patent
Dietz et al.

(10) Patent No.: US 7,470,288 B2
(45) Date of Patent: Dec. 30, 2008

(54) TELEMETRIC TIBIAL TRAY

(75) Inventors: Terry Dietz, Columbia City, IN (US); Mark DiSilvestro, Fort Wayne, IN (US); Bob Hastings, Warsaw, IN (US); Frank D. Matthews, Walpole, MA (US); Tony Petrella, Fort Wayne, IN (US); John E. Slamin, Wrentham, MA (US); Paul Tomaszewski, Columbia City, IN (US)

(73) Assignee: DePuy Products, Inc., Warsaw, IN (US)

( * ) Notice: Subject to any disclaimer, the term of this patent is extended or adjusted under 35 U.S.C. 154(b) by 586 days.

(21) Appl. No.: 10/814,953

(22) Filed: Mar. 31, 2004

(65) Prior Publication Data

US 2005/0010302 A1    Jan. 13, 2005

Related U.S. Application Data

(60) Provisional application No. 60/486,615, filed on Jul. 11, 2003, provisional application No. 60/486,762, filed on Jul. 11, 2003, provisional application No. 60/486,614, filed on Jul. 11, 2003.

(51) Int. Cl.
*A61F 2/38*    (2006.01)
*A61B 5/103*    (2006.01)

(52) U.S. Cl. .................. 623/20.14; 623/20.32; 600/587

(58) Field of Classification Search ................ 600/595, 600/587; 606/102; 623/20.14, 20.15, 20.21, 623/20.34, 20.35, 20.36; 73/862.632, 862.045, 73/862.046

See application file for complete search history.

(56) References Cited

U.S. PATENT DOCUMENTS 3,456,226 A * 7/1969 Vick .............................. 338/2

(Continued)

FOREIGN PATENT DOCUMENTS

WO    WO 00/65981    11/2000

(Continued)

OTHER PUBLICATIONS

Seedhom et al., *A Technique for the Study of Geometry and Contact in Normal and Artificial Knee Joints*, 1972, Wear—Elsevier Sequoia S.A. Lausanne—Printed in the Netherlands, pp. 189-199.

(Continued)

*Primary Examiner*—Pedro Philogene
(74) *Attorney, Agent, or Firm*—Maginot, Moore & Beck

(57) ABSTRACT

A telemetric tibial tray includes a lower plate that defines a plurality of cylindrical transducer cavities having circular load diaphragms. An upper plate is attached to the lower plate through support posts projecting from the load diaphragms. The support posts have a circular cross-section and a diameter of about 5.0 mm. The lower plate further defines wiring channels communicating between the transducer cavities and a central cavity housing the circuit board for the telemetric tray. The wiring channels are arranged at a 45 degree angle relative to the sagittal plane of the knee joint in order to reduce the effects of the wiring channel intersection on the strain sensitivity of the tray. Each transducer cavity includes a radial strain gage array with four pairs of radially aligned strain gages, each pair aligned at a 45 degree angle relative to the sagittal plane of the knee joint. Each pair of strain gages includes an inner gage positioned at the point of maximum positive micro-strain across the diaphragm when loaded, and an outer gage positioned at the point of maximum negative micro-strain, to thereby increase the differential strain measured by the gages and increase the strain sensitivity of the tibial tray.

13 Claims, 3 Drawing Sheets

U.S. PATENT DOCUMENTS

| | | | |
|---|---|---|---|
| 4,024,588 A | | 5/1977 | Janssen et al. |
| 4,045,825 A | | 9/1977 | Stroot |
| 4,675,670 A | | 6/1987 | Lalonde et al. |
| 4,950,986 A | | 8/1990 | Guerrero |
| 5,113,869 A | | 5/1992 | Nappholz et al. |
| 5,197,488 A | * | 3/1993 | Kovacevic .................. 600/595 |
| 5,300,120 A | | 4/1994 | Knapp et al. |
| 5,360,016 A | * | 11/1994 | Kovacevic .................. 600/595 |
| 5,365,799 A | * | 11/1994 | Okada ................... 73/862.041 |
| 5,376,128 A | | 12/1994 | Bozeman |
| 5,395,033 A | | 3/1995 | Byrne et al. |
| 5,458,655 A | | 10/1995 | Bozeman |
| 5,465,619 A | | 11/1995 | Sotack et al. |
| 5,470,354 A | | 11/1995 | Hershberger et al. |
| 5,480,454 A | | 1/1996 | Bozeman |
| 5,518,008 A | | 5/1996 | Cucchiaro et al. |
| 5,609,643 A | | 3/1997 | Colleran et al. |
| 5,769,875 A | | 6/1998 | Peckham et al. |
| 5,776,171 A | | 7/1998 | Peckham et al. |
| 5,780,749 A | * | 7/1998 | Okada ................... 73/862.043 |
| 5,831,430 A | | 11/1998 | Pfanstiehl et al. |
| 5,935,171 A | | 8/1999 | Schneider et al. |
| 5,954,758 A | | 9/1999 | Peckham et al. |
| 6,026,328 A | | 2/2000 | Peckham et al. |
| 6,155,267 A | | 12/2000 | Nelson |
| 6,163,725 A | | 12/2000 | Peckham et al. |
| 6,228,900 B1 | | 5/2001 | Shen et al. |
| 6,245,109 B1 | | 6/2001 | Mendes et al. |
| 6,272,379 B1 | | 8/2001 | Fischell et al. |
| 6,281,264 B1 | | 8/2001 | Salovey et al. |
| 6,281,679 B1 | | 8/2001 | King et al. |
| 6,332,089 B1 | | 12/2001 | Acker et al. |
| 6,400,989 B1 | | 6/2002 | Eckmiller |
| 6,402,689 B1 | | 6/2002 | Scarantino et al. |
| 6,442,413 B1 | | 8/2002 | Silver |
| 6,447,448 B1 | | 9/2002 | Ishikawa et al. |
| 6,454,781 B1 | | 9/2002 | Witt et al. |
| 6,473,652 B1 | | 10/2002 | Sarwa et al. |
| 6,498,944 B1 | | 12/2002 | Ben-Haim et al. |
| 6,506,216 B1 | | 1/2003 | McCue et al. |
| 6,507,189 B2 | | 1/2003 | Woolsey et al. |
| 6,558,229 B2 | | 5/2003 | Kimura et al. |
| 6,563,308 B2 | | 5/2003 | Nagano et al. |
| 6,573,706 B2 | | 6/2003 | Mendes et al. |
| 6,583,630 B2 | | 6/2003 | Mendes et al. |
| 6,679,920 B2 | | 1/2004 | Biedermann et al. |
| 6,689,056 B1 | | 2/2004 | Kilcoyne et al. |
| 6,890,303 B2 | | 5/2005 | Fitz |
| 6,917,831 B2 | | 7/2005 | Bloemer et al. |
| 7,179,295 B2 | * | 2/2007 | Kovacevic ............... 623/17.15 |
| 2001/0000187 A1 | | 4/2001 | Peckham et al. |
| 2002/0133175 A1 | | 9/2002 | Carson |
| 2002/0147455 A1 | | 10/2002 | Carson |
| 2003/0069644 A1 | * | 4/2003 | Kovacevic et al. ........ 623/20.32 |
| 2004/0019384 A1 | | 1/2004 | Kirking et al. |
| 2004/0034355 A1 | | 2/2004 | Govari et al. |
| 2004/0243148 A1 | | 12/2004 | Wasielewski |

FOREIGN PATENT DOCUMENTS

| WO | WO 2005-055871 | 6/2005 |
|---|---|---|
| WO | WO 2005/055871 | 6/2005 |

OTHER PUBLICATIONS

Troyk et al., *Design and Implementation of an Implantable Goniometer*, IEEE Transactions on Biomedical Engineering, Feb. 1986, pp. 215-222, vol. BME-33, No. 2.

Selvik, *Roentgen stereophotogrammetry A method for the study of the kinematics of the skeletal system*. Acta Orthopaedica Scandinavica, 1989, pp. 1-51, Supplementum No. 232, vol. 60, Munksgard Copenhagen.

Graichen et al., *Four-Channel Telemetry System for In Vivo Measurement of Hip Joint Forces*, J. Biomed. Eng., Feb. 1991, pp. 370-374, vol. 13.

Pavelka et al., *Correlation between knee roentgenogram changes and clinical symptoms in osteoarthritis*; Rev. Rhum. Mal. Osteoartic., Apr. 1992, pp. 553-559, 59 (9).

Graichen et al., *Inductively Powered Telemetry System for In Vivo Measurement with Orthopaedic Implants*, Biotelemetry XIII, Mar. 26-31, 1995—Williamsburg, VA, pp. 75-80.

Conrozier et al., *Quantitative radiography in osteoarthritis: Computerized measurement of radiographic knee and hip joint space* Baillière's Clinical Rheumatology, Aug. 1996, pp. 429-433, vol. 10, No. 3, Copyright © 1996, by Baillière's Tindall.

Karrholm et al; *Radiosterometry of Hip Prostheses Review of Methodology and Clinical Results*, Clinical Orthopaedics and Related Research, 1997, pp. 94-110, No. 344.

Ilchmann, *Thesis Radiographic assessment of cup migration and wear after hip replacement*, Acta Orthopaedica Scandinavica, Oct. 1997, pp. 1-27, vol. 68, Supplementum No. 276.

Lanyon et al; *Radiographic assessment of symptomatic knee osteoarthritis in the community: definitions and normal joint space*. Ann Rheum Dis, Aug. 1998, pp. 595-601, No. 57.

Vrooman et al., *Fast and accurate automated measurements in digitized stereophotogrammetric radiographs*. Journal of Biomechanics, 1998, pp. 491-498, 31.

Önsten et al; *Wear in uncemented porous and cemented polyethelene sockets, A Randomised, Radiosterometric Study*, The Journal of Bone and Joint Surgery, Mar. 1998, pp. 345-350, 80(2).

Johnson et al; *Implantable Transducer for Two-Degree of Freedom Joint Angle Sensing*. IEEE Transactions on Rehabilitation Engineering, Sep. 1999, pp. 349-359, vol. 7, No. 3.

Miller et al., *Molecule-Based Magnets—An Overview*. MRS Bulletin, Nov. 2000, pp. 21-28.

Ryd et al., *Methods for determining the accuracy of radiostereometric analysis (RSA)*, Acta Orthopaedic Scandinavica, 2000, pp. 403-408, 71 (4). © Taylor & Francis 2000.

Cicuttini et al., *Tibial and femoral cartilage changes in knee osteoarthritis*, Ann Rheum Dis, Oct. 2001; pp. 977-980, 60.

Hyldahl et al., *Does Metal Backing Improve Fixation of Tibial Component in Unicondylar Knee Arthroplasty? A Randomized Radiosterometric Analysis*, The Journal of Arthroplasty, 2001, pp. 174-179, vol. 16 No. 2.

Sychertz et al., *Effect of Radiographic Quality on Computer-Assisted Head Penetration Measurements*, Clinical Orthopaedics and Related Research, 2001, pp. 150-158, No. 386.

Bhadra et al., *Implementation of an Implantable joint-angle Transducer* Journal of Rehabilitation Research and Development, May/Jun. 2002, pp. 411-422, vol. 39, No. 3.

Bragdon et al., *Experimental assessment of precision and accuracy of radiostereometric analysis for the determination of polyethylene wear in a total hip replacement model*, Journal of Orthopaedic Research, 2002, pp. 688-695, © 2002 Orthopaedic Research Society, Published by Elsevier Science Ltd.

Hilliquin et al., *Quantitative assessment of joint space width with an electronic caliper*. Osteoarthritis and Cartilage, 2002, pp. 542-546, 10.

European Search Report for European Application No. 05251832.1-2310 PCT/ dated Aug. 5, 2004, 4 pages.

* cited by examiner

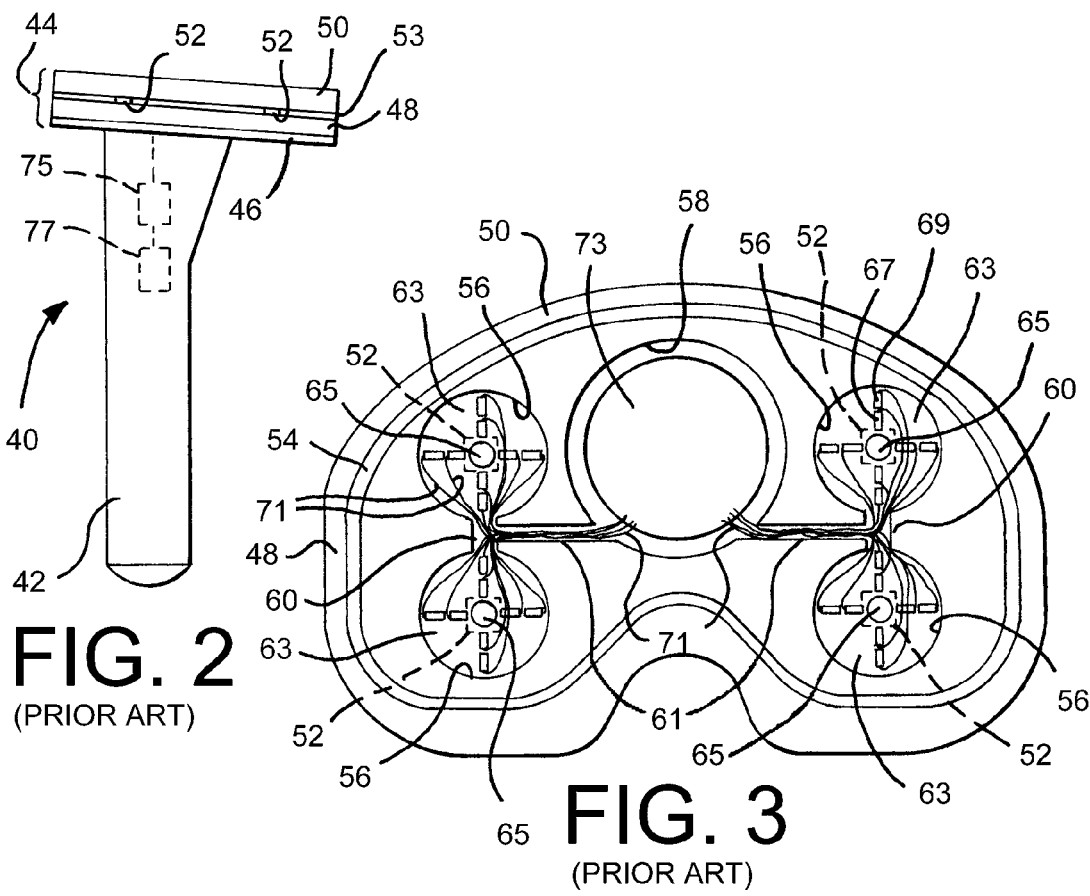
FIG. 2 (PRIOR ART)
FIG. 3 (PRIOR ART)
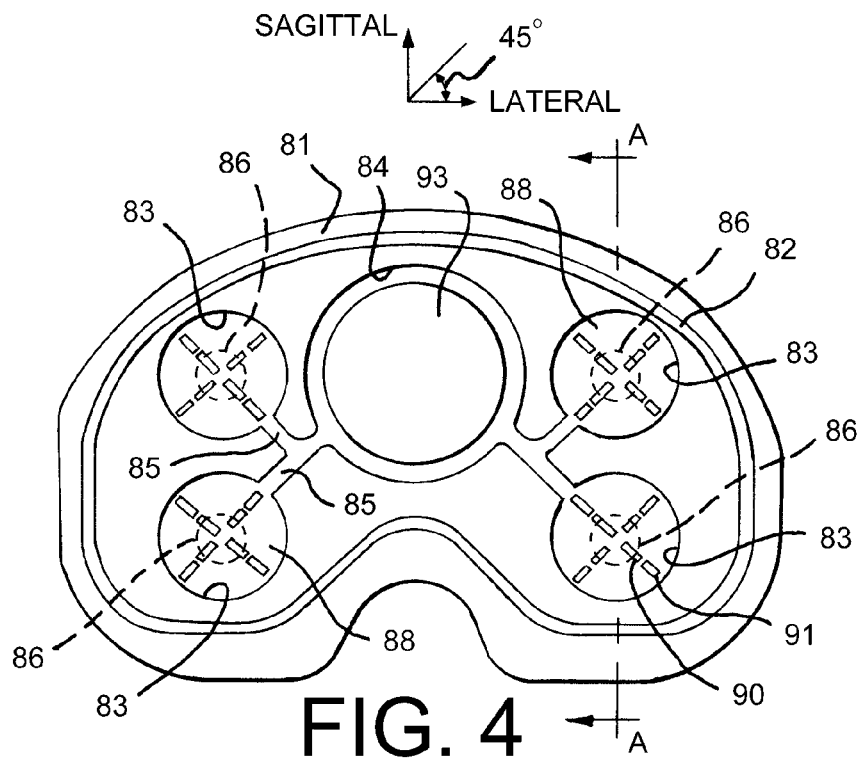
FIG. 4

US 7,470,288 B2

TELEMETRIC TIBIAL TRAY

CROSS-REFERENCE TO RELATED APPLICATIONS

This application claims priority to the following U.S. Provisional Patent Applications: Ser. No. 60/486,615, entitled "In Vivo Joint Space Measurement Device and Method", filed on Jul. 11, 2003, and naming one of the co-inventors of the present application; Ser. No. 60/486,762, entitled "In Vivo Joint Implant Cycle Counter", filed on Jul. 11, 2003, and naming one of the co-inventors of the present application; and Ser. No. 60/486,614, entitled "Orthopaedic Element With Self-Contained Data Storage", filed on Jul. 11, 2003, and naming co-inventors of the present application. The disclosure of each of these provisional applications (60/486,615; 60/486,762; and 60/486,614) is incorporated herein by reference.

FIELD OF THE INVENTION

The present invention relates to orthopaedic components configured for implantation within a patient. In particular, the invention concerns systems and methods for evaluating loads within a joint space, and more particularly in the knee.

BACKGROUND OF THE INVENTION

Joint replacement surgery is quite common and enables many individuals to function normally when otherwise it would not be possible to do so. Artificial joints are normally composed of metallic and/or ceramic components that are fixed to existing bone.

Knee arthroplasty is a well known surgical procedure by which a diseased and/or damaged natural knee joint is replaced with a prosthetic knee joint. Typical knee prostheses include a femoral component, a patella component, a tibial tray or plateau, and a tibial bearing member. The femoral component generally includes a pair of laterally spaced apart condylar portions, the inferior or distal surfaces of which articulate with complementary condylar elements formed in a tibial bearing component.

In a properly functioning artificial knee joint, the condylar portions of the femoral component must slide and roll freely over the articulation surface formed by the condylar elements of the tibial bearing member. Natural friction within a replaced, artificial joint can lead to the development of wear debris in which minute particles of debris (e.g., metal or plastic from the prosthesis) become dislodged and migrate within the joint. The phenomenon of wear debris within artificial joints is a serious problem that can inhibit the proper mechanical functioning of the joint. Moreover, wear debris can lead to osteolysis and bone deterioration. When wear debris develops within an artificial joint, surgical removal of the debris or subsequent replacement of the artificial joint is often necessary.

During normal usage of a properly implanted prosthetic knee joint, load and stress are placed on the tibial bearing member. The tibial bearing member is typically made of an ultrahigh molecular weight polyethylene (UHMWPE), and friction, continuous cycling and stress can cause some erosion and/or fracture of the tibial bearing member, thus leading to wear debris. The risk of wear debris can be even greater during malalignment of an artificial knee joint, which can result from normal usage or from imperfect and/or inaccurate implantation of the prosthesis within a patient. During malalignment the load upon the tibial bearing member is not evenly distributed. Instead, excess load is placed on certain areas of the tibial bearing member. This uneven distribution of load (or edge loading) can accelerate the development of wear debris. Contact stresses on the tibial bearing member increase substantially with malalignment of the joint, thus increasing the risk that wear debris will develop when a prosthetic knee joint is subjected to malalignment conditions.

Joint replacement surgery obviously requires a tremendous degree of precision to ensure that prosthetic components are properly sized, implanted, and aligned. Imperfect sizing, implantation and alignment can lead to inadequate performance of the knee joint as well as to the presence of high contact stresses in certain areas of the prosthesis, thus leading to the possible development of wear debris.

The anatomy of patients who undergo knee arthroplasty is widely variable and can lead to difficulty in matching the standard sized prosthetic components that form a prosthetic joint. Many prosthetic components are manufactured such that similarly sized components must be used together and implanted within a patient when replacing a natural joint. That is, the femoral component, tibial bearing member, and tibial plateau that form the artificial knee joint must normally be of a matched size. If the components are not size-matched, inappropriate edge loading may develop and accelerate wear.

FIG. 1 illustrates three components found in a typical knee joint prosthesis 10. A femoral component 12 includes a superior surface 14 which is mountable within the distal end of a patient's femur and an inferior articulation surface 16. The articulation surface 16 includes adjacent condyles 18. The knee prosthesis 10 also includes a tibial tray or plateau 20 which includes a distally extending stem 22 that is mountable within the tibia of a patient. The proximal end of the tibial tray 20 includes a recessed region 24 within which a tibial bearing member 26 is mounted in a mechanical fit.

Tibial bearing member 26 includes a distal surface 30 mountable within the recessed region 24 of the proximal end of a tibial tray 20 plateau 24. The proximal face of tibial bearing member 26 forms articulation surfaces 28 that engage and articulate with the articulation surfaces 16 of femoral component 12. The articulation surfaces 28 of the tibial bearing member 26 are configured to correspond to the condyles 18 of the femoral component 12.

The articulation surface 16 of femoral component 12 and the articulation surfaces 28 of tibial bearing member 26 are configured such that the contact area is maximized. The greatest contact area is achieved in conditions of perfect alignment throughout the range of motion of the knee joint, and in certain conditions of malalignment, including varus-valgus lift and internal-external rotation. The ability to achieve a large contact area between the articulating surfaces is significant because contact stress on the prosthesis components is minimized, particularly the tibial bearing member. Most standard tibial bearing members are manufactured of polymeric materials, such as ultra-high molecular weight polyethylene (UHMWPE), ceramic or metal. Where loads are unevenly distributed or concentrated across the tibial bearing member during use of an artificial knee joint, edge loading can develop. Edge loading leads to the development of higher contact stresses in certain parts of the prosthesis which, in turn, can cause wear of the articulating surfaces. Debris resulting from this wear can develop within the joint, sometimes leading to osteolysis.

More significantly, undue bearing wear can result in conditions requiring that the joint endoprosthesis be removed and replaced in a revision procedure. Accordingly, early determination of unacceptable wear conditions is critical. Misalignment of the joint prosthesis components can be detected during the implantation procedure and during rehabilitation of the new joint. Various measurements and templates can evaluate proper positioning and spacing of the components.

Another important indicator of proper or improper alignment is the distribution and transfer of loads across the prosthesis. In particular, loads experienced by the tibial tray 20 can provide the earliest indication of bad joint "fit". In order to evaluate these loads, telemetric implant components have been developed, such as the dual tray telemetric implant described in U.S. Pat. No. 5,360,016 ("016 patent"), the disclosure of which is incorporated herein by reference. A force transducer is incorporated into the proximal tibial component of the implant. The force transducer uses strain gages to generate output signals indicative of force measurement data that can be used to assess pressure differences across the surface of the tibial tray which may be indicative of an improperly aligned implant.

Another telemetric implant is embodied in a tibial component 40 depicted in FIGS. 2 and 3. The tibial component 40 includes a stem 42 configured to be engaged within the tibia. A tibial tray 44 is mounted on the stem, and includes a cover plate 46 that is directly attached to the stem. A lower plate 48 is mounted on the cover plate, while an upper plate 50 is supported on the lower plate by a plurality of support posts 52. As best seen in FIG. 3, the lower plate 48 includes a perimeter wall 54 configured to engage the cover plate 46. Fasteners (not shown) are used to fasten the two plates together.

The lower plate defines a plurality of transducer cavities 56, each corresponding to a support post. The base of each cavity defines a diaphragm 63 to which a corresponding support post 52 is attached or integrally formed. The support posts are preferably integral with the lower plate 48 and the upper plate 50 but are configured to separate the two plates by a gap 53. Load applied to the upper plate 50 is transmitted through the support posts 52 to the integral diaphragms 63 which flex in relation to the transmitted load.

In order to measure the deflection of these diaphragms, a force sensing element is disposed within each transducer cavity. More specifically, the force sensing elements include an array of strain gages that are affixed to the diaphragm at the base of each transducer cavity 63. As shown in FIG. 3, each strain gage array includes four radially inner strain gages 67 and four radially outer gages 69 disposed at the four compass points around the cavity. More specifically, the strain gages are arranged in planes that are at 90 degrees or 180 degrees to the sagittal and/or lateral planes of the knee joint prosthesi.

The strain gages include wiring 71 that passes through wiring channels 60 and 61 to a centrally located circuitry cavity 58. A processing circuit board 73 is disposed within this cavity and includes electrical components and/or integrated circuits adapted to process the output of the strain gages and facilitate translation of that output into load information. In some implants, such as the force transducer disclosed in the '016 patent incorporated above, the circuit board 73 serves to condition the strain gage signals and to provide a wiring harness for connection to an external processor or computer. In other implants, the circuit board 73 prepares the strain gage signals for transmission by a transmission device. In some implants, the circuit board includes a telemetry device and a power supply. In other implants, the stem 42 (FIG. 2) carries a telemetry device 75 and associated power source 77 adapted to transmit the strain gage output signals to an external processor where the signals are evaluated.

In the telemetric tibial component 40 shown in FIG. 3, a no-load post 65 projects from the diaphragm 63 between the inner strain gages 67. It can be appreciated that the no load posts 65 are essentially co-linear with the support posts 52, although the two sets of posts reside on opposite sides of the diaphragm 63 of each transducer cavity 56. The no-load posts are believed to promote a circumferentially symmetric strain pattern within each cavity.

The introduction of telemetric implants has provided a means for evaluating the loads actually experienced by an endoprosthesis. This evaluation can occur in real-time as the joint is exercised and loaded. However, since the primary function of the implant is to serve as a prosthetic joint, and not simply as a data transmission device, the implant must be able to withstand joint loads without failure. Load is transmitted from the femur to the tibia through the large articulating surface areas of the condylar surfaces 16 and the bearing surfaces 28. However, once the load reaches the tibial tray, such as the tibial tray 44, the force is transmitted through four support posts 52 into the tibia. Therefore, it can be appreciated that the strength of these posts is critical to the strength of the implant.

In conflict with need for structural strength is the need to generate sufficient strain in the diaphragms 63 such that a measurable strain differential may be detected between the strain gages 67 and 69. The ability to accurately measure the forces transmitted across the joint space is enhanced as the magnitude of the strain differential increases. The trade-off for a stronger implant has been a reduction in diaphragm strain and a sacrifice in accuracy of the load measurement. The introduction of the no-load posts 65 is an effort to recapture some accuracy in the load measurement capabilities of the strain gage arrays. There remains room for improvement in both the strength of the telemetric implant component as well as the ability of the transducer component to provide a true measure of the loads transmitted across the joint.

SUMMARY OF THE INVENTION

The telemetric tibial tray of the present invention provides an optimum balance of implant strength and accuracy in load measurement. In accordance with one embodiment of the invention, the cross-sectional area of the support posts is increased over the prior art devices. Moreover, in lieu of the square cross-section of the prior art support posts, the support posts in the present invention are circular, which maximizes the load-bearing area of the posts without sacrificing flex responsiveness of the load diaphragm to which the posts are attached.

In another feature of the invention, the no-load post is eliminated so that the cavity-side face of the load diaphragm is featureless. Removing the no-load posts eliminates stress risers at the junction between the no-load posts and the diaphragms and significantly reduces the risk of fracture at the base of the support posts.

In addition, removing the no-load posts allows repositioning of the strain gage array from the pattern employed in the prior art. It has been found that the radial strain pattern across the load diaphragm exhibits significant micro-strain behavior at the center of the diaphragm. Removing the no-load posts allows placement of the radially inboard strain gages as close to the center of the diaphragm as possible. At each circumferential position, there is more room for the radially outermost strain gage so that the two strain gages at each circumferential position yield a more accurate differential strain reading, which translates into a more accurate measure of the diaphragm strain.

The radial position of the inner and outer strain gages is also calibrated according to the micro-strain response of the transducer cavity diaphragm to load. In one aspect of the invention, the inner strain gage is positioned to span the radial location at which the maximum positive micro-strain occurs. The outer strain gage is positioned at a radial location between the zero crossing point and the outer wall of the cylindrical transducer cavity. In a more specific aspect, the outer strain gage is positioned to span the radial location of the maximum negative micro-strain response of the diaphragm. These optimized locations produce the greatest differential strain value, which leads to greater strain sensitivity of the force measurement features of the invention.

Another aspect of the strain gage pattern diverges from the compass point arrangement of the prior art telemetric implants. Rather than align the radial strain gages in planes parallel to the sagittal and lateral planes through the joint, the strain gages of the present invention are rotated at 45 degrees. It has been found that this orientation of the radial strain gages increases the strain sensitivity of the transducer component, especially when the joint is flexed or extended.

A further improvement provided by the present invention is in the location of the wiring channels in the tibial tray. The wiring channels, although necessary for connection of the strain gage wiring to the central circuit board, disrupt the transducer cavities and produce non-uniform strain patterns across the load diaphragm. In accordance with one feature of the invention, the wiring channels intersecting each transducer cavity is at a 45 degree angle relative to the sagittal and lateral planes. It has been found that this positioning of the wiring channels also increases the strain sensitivity of the transducer.

It is one object of the present invention to provide a telemetric tibial tray that has increased strength characteristics over prior telemetric components. Another object is to increase the strain sensitivity of the telemetric component over prior devices. These and other objects, as well as specific benefits, of the present invention will be appreciated upon consideration of the written description and accompanying figures.

DESCRIPTION OF THE FIGURES

FIG. 2 is a side view of a tibial component of a knee prosthesis.

FIG. 3 is a bottom view of a lower transducer plate forming part of the tibial component shown in FIG. 2.

FIG. 4 is a bottom view of a lower transducer plate for a telemetric tibial tray in accordance with one embodiment of the present invention.

DESCRIPTION OF THE PREFERRED EMBODIMENTS

Figure 1:
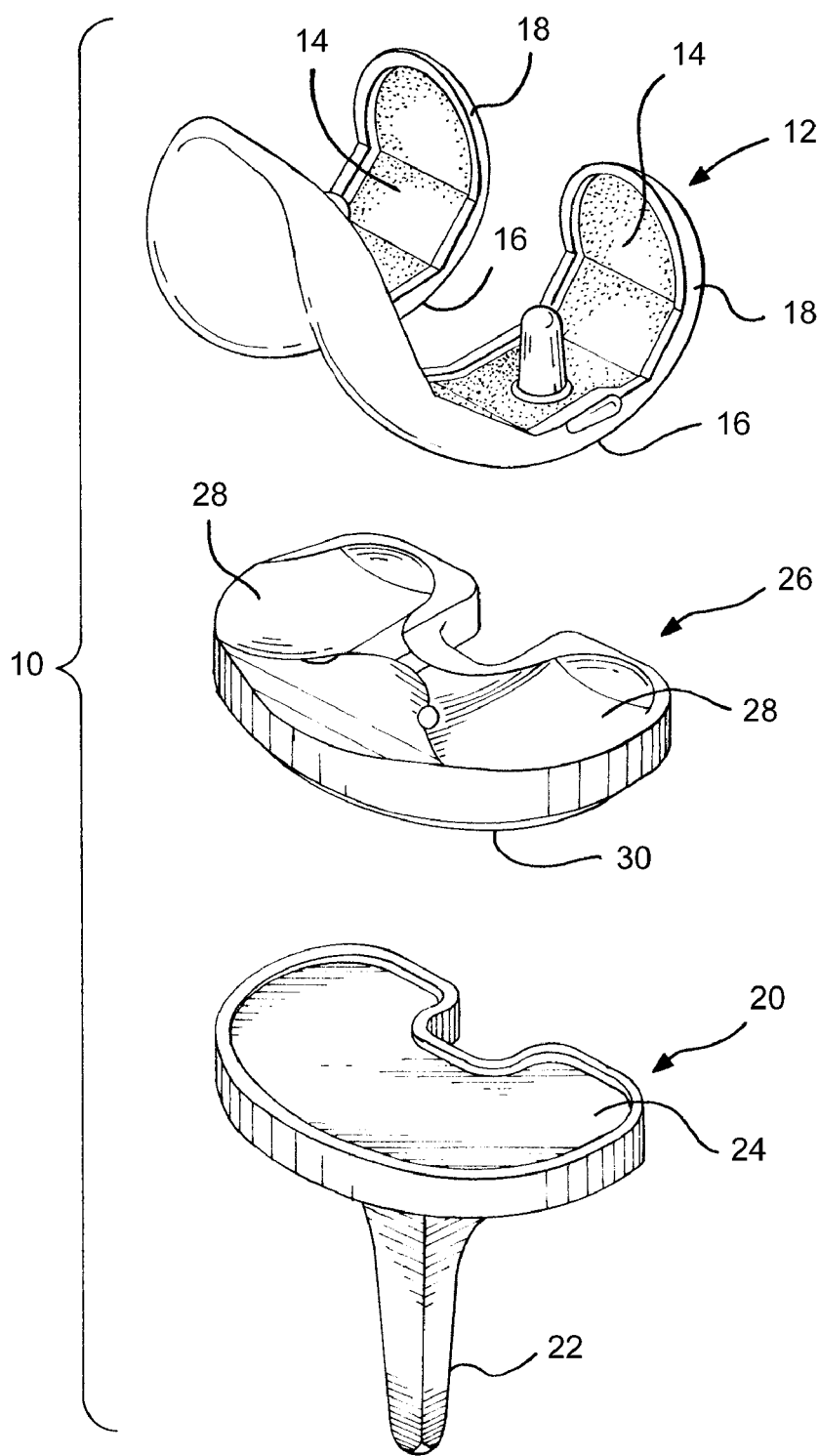
FIG. 1 is an exploded perspective view of the components of a knee prosthesis.

For the purpose of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

As shown in FIG. 3, the lower transducer plate 48 of prior telemetric tibial trays utilizes support posts 52 that are square in cross-section. These support posts typically have a dimension of about 2.5 mm on each side. Each support post is integral with the load diaphragm 63 and is aligned with the no-load post 65 projecting into the transducer cavity. The no-load posts produce stress risers at the junction with the load diaphragm. The strain pattern across the diaphragm is disrupted by the presence of the no-load posts.

Moreover, the posts 65 limit the radial space available in the cavity 56 for placing the radial strain gages 67, 69. In prior devices, two strain gages are placed diametrically opposite each other, as reflected in the '016 patent incorporated above. In later devices, two strain gages have been placed along each radial extent to measure the differential strain at different circumferential positions around the diaphragm. The presence of the no-load posts 65 in these prior devices limits the space available for the radial strain gage pairs.

In the prior devices, such as the tibial component 40 illustrated in FIG. 3, the strain gage pairs are aligned along the compass points. More succinctly, the strain gages are positioned in planes that are parallel with the sagittal and lateral planes of the joint. Similarly, the wiring channels 60, 61 of the prior device 40 are also aligned with the sagittal and lateral planes. The wiring channels interrupt the transducer cavity and disrupt the strain sensitivity at that intersection.

Figure 5:
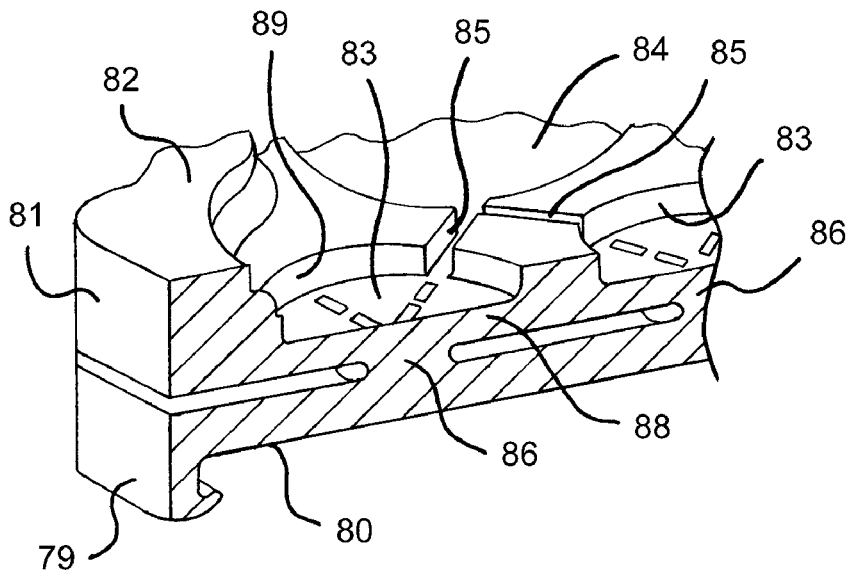
FIG. 5 is a partial cross-sectional view of the lower transducer plate shown in FIG. 4.

The present invention provides significant improvements over the tibial component 40 and addresses certain limitations of this component discussed above. Referring to FIGS. 4 and 5, a lower plate 81 is provided as part of a telemetric tibial tray. The lower plate 81 and an integral upper plate 79 (FIG. 5) can be substituted for the like components of the tibial tray 44 shown in FIG. 2. Thus, the lower plate 81 defines a perimeter wall 82 that is configured to engage the cover plate 46 so that the cover plate can shield the electrical components carried by the lower plate. The upper plate 79 includes a recess 80 configured to receive the tibial bearing member 26 depicted in FIG. 1.

As with the prior art devices, the lower plate 81 includes a plurality of cylindrical transducer cavities 83 and a centrally located circuitry cavity 84. The upper and lower plates are integrally attached by four support posts 86 projecting from a circular load diaphragm 88 in each transducer cavity. As understood, the diaphragms 88 flex when subjected to forces transmitted through the support posts 86. However, unlike the prior art, the support posts have a circular cross-section, as best seen in FIG. 4. Moreover, the cross-sectional area of these support posts 86 is significantly increased over the support posts of the prior art, such as the square posts shown in FIG. 3. In the preferred embodiment of the invention, the support posts 86 have a diameter of about 5.0 mm. The cross-sectional area of these posts is about 20 mm$^2$, which is over three times larger than the cross-sectional area (6.25 mm$^2$) of the prior devices. This significantly greater cross-sectional area means that the support posts 86 have greater load bearing capacity with a longer fatigue life than the prior devices. In a preferred embodiment of the invention, the diameter of the support posts is about ⅓ the diameter of the transducer cavity.

In a further feature of the invention, the load diaphragm 88 does not include a no-load post at the center of the diaphragm. Eliminating the no-load posts found in the prior devices (see FIG. 3) eliminates the stress risers and the potential locus for fatigue that accompanies those load posts. Moreover, removing the no-load posts frees the center of the diaphragm for an optimum placement of radial strain gages around the transducer cavities 83.

Figure 6:
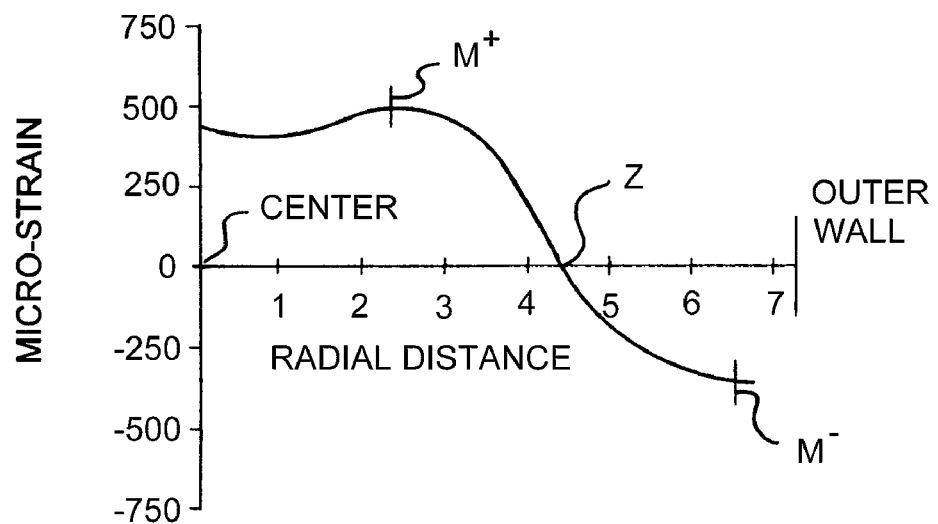
FIG. 6 is a graph of micro-strain as a function of radial distance in a transducer cavity of the plate shown in FIG. 4.

Turning to the graph of FIG. 6, it can be seen that the micro-strain as a function of radial distance exhibits a high response at the center of the load diaphragm 88. The micro-strain remains at this high level for about half the radial distance to the perimeter of the transducer cavity and exhibits a positive maximum value at a radial location $M^+$ offset from the center of the diaphragm. The zero-crossing represents the point at which the micro-strain reverses sign from a positive magnitude to a negative magnitude. The zero crossing point Z for the micro-strain is nearer the radial edge of the cavity. The micro-strain response of the diaphragm also exhibits a negative maximum value point $M^-$ between the zero crossing point and the outer wall 89 of the cylindrical cavity. This strain graph provides a guideline for optimum placement of the force sensing elements within the cavities, or more particularly the radial strain gages, namely the inner gages 90 and radially outer gages 91.

As is known in the art, the strain gage array measures differential strain across the diaphragm, which can then be translated directly into a measure of the forces imposed on the diaphragm as the knee prosthesis is loaded. Depending upon the arrangement of the array, the measured strains can be used to calculate the load imposed on the tibial tray, including its magnitude, direction and location. These calculations can be made in an external processor, such as a computer, upon receiving the data transmitted form the telemetric implant in a known manner. As is known in the art, providing a cylindrical transducer cavity and circular load diaphragm allows placement of the strain gages in a circumferential pattern about the center of the diaphragm to evaluate the radial differential strain across the diaphragm.

Increasing the strain sensitivity of the strain gage array will produce a more accurate measure of the differential strain at various points around the load diaphragm. It has been found in accordance with the present invention that placing the radially inner strain gages 90 close to the center of the diaphragm increases the strain sensitivity of the gage array. In a preferred embodiment, the inner gages are positioned to span the maximum micro-strain point $M^+$, which in a specific embodiment is within 2.5 mm of center. Removal of the no-load post allows this more radially inboard position for the inner strain gage.

In addition, the present invention contemplates positioning the outer strain gages as close as possible to or immediately adjacent the outer wall 89 (FIG. 5) of the cylindrical cavity 83. With this position, the outer gages 91 will be positioned beyond the zero crossing point Z for the micro-strain across the diaphragm. Preferably, the outer gage is positioned to span the negative maximum micro-strain point $M^-$. This placement of the inner and outer strain gages 90, 91 produces the largest differential strain, and consequently the greatest strain sensitivity. As an additional improvement, the diameter of the transducer cavities is increased from the prior art devices. Specifically, the diameter is increased from 13.4 mm to about 15.0 mm. This larger diameter provides more radial space for placement of the outer strain gage 91, which assures that the outer gage will be well beyond the zero-crossing for the micro-strain, as reflected in the graph of FIG. 6. The larger diameter transducer cavity consequently yields greater differential strain values, which improves the accuracy of the load measurements.

The preferred embodiment of the invention yields even greater improvements in load measurement accuracy by optimizing the orientation of the strain gage arrays. It has been found that rotating the diametrically opposed inner/outer gage pairs by 45 degrees further increases measurement sensitivity. Thus, as shown in FIG. 4, the inner and outer gages 90, 91, respectively, are arranged at a 45 degree angle relative to the sagittal and lateral planes. Rotating the position of the radial strain gage pairs increases the differential strain measured between the inner and outer gages, relative to the conventional placed gages of the prior art. Again, increases in differential strain translate directly into more accurate load measurements in each load diaphragm.

Additional improvement is realized by orienting the strain gages at a 45 degree angle relative to the wiring channels. In one embodiment of the invention, the strain gages 90, 91 are oriented as shown in FIG. 4, while the wiring channels 60 are oriented as shown in FIG. 3. In other words, the wiring channels are arranged at 90 or 180 degrees relative to the sagittal plane for the joint or prosthesis, while the strain gages 90, 91 are oriented at 45 or 135 degrees to the same plane. Thus, with this specific embodiment, no strain gage is aligned with the interface between a transducer cavity and a wiring channel.

In another aspect of the invention, arrangement of the wiring channels was also found to contribute to the strain sensitivity of the telemetric tibial tray. The wiring channels 85 provide a path for the strain gage wiring to connect to the circuit board 93 disposed within the central cavity 84. (Note that the wires are not depicted within the channels 85 in FIG. 4 for clarity). It can be appreciated that the intersection of a wiring channel with the transducer cavity creates a localized disruption in the strain pattern across the diaphragm 88; however, the wiring channels are necessary (absent the cost-prohibitive approach of burying the wires within the body of the lower plate 81). The present invention contemplates optimum positioning of the wiring channels at 45 degrees to the sagittal and lateral planes, as illustrated in FIG. 4. This orientation of the wiring channel produces greater differential strains than the prior conventional channel placement.

With the wiring channel arrangement shown in FIG. 4, it is preferable that the strain gages be oriented at an offset angle relative to the channels. In other words, it is preferable that no strain gage be aligned with the intersection between a wiring channel and a corresponding transducer cavity. Thus, in a specific embodiment, the wiring channels 85 are angularly oriented as shown in FIG. 4 at a 45 or 135 degree angle relative to the sagittal plane, while the strain gages can be arranged like the gages 67, 69 shown in FIG. 3 at 0 or 180 degrees relative to the same plane. In certain alternatives, improvements in differential strain sensitivity may still be accomplished if the strain gages and wiring channels are both oriented at the 45 and 135 degree angles.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. In a telemetric knee prosthesis adapted to measure forces transmitted across the knee joint, the knee prosthesis having a femoral component, a tibial bearing member in articulating contact with the femoral component, a tibia engaging member and a tibial tray engaged to the tibial bearing member and the tibia engaging member, the tibial tray comprising:

an upper plate having a portion configured for engaging the tibial bearing member;

a lower plate having a portion configured for engaging the tibia engaging member, said lower plate spaced apart from said upper plate and defining a plurality of cavities opening away from said upper plate, each of said cavities including a diaphragm adapted to flex when subjected to a load normal to the diaphragm;

a plurality of support posts, each connected between said upper plate and said diaphragm of a corresponding one of said plurality of cavities, wherein said support posts are circular in cross-section and have a diameter that is about ⅓ the diameter of the corresponding one of said plurality of cavities; and a force sensing element disposed within each of said plurality of cavities and operable to produce an output signal in response to flexing of said diaphragm.

2. The tibial tray of claim 1, wherein said support posts each have a diameter of about 5.0 mm.

3. In a telemetric knee prosthesis adapted to measure forces transmitted across the knee joint, the knee prosthesis having a femoral component, a tibial bearing member in articulating contact with the femoral component, a tibia engaging member and a tibial tray engaged to the tibial bearing member and the tibia engaging member, the tibial tray comprising:

an upper plate having a portion configured for engaging the tibial bearing member;

a lower plate having a portion configured for engaging the tibia engaging member, said lower plate spaced apart from said upper plate and defining a plurality of cylindrical cavities opening away from said upper plate, each of said plurality of cylindrical cavities including a circular diaphragm adapted to flex when subjected to a load normal to the diaphragm and an outer wall;

a plurality of support posts, each connected between said upper plate and said diaphragm of a corresponding one of said plurality of cylindrical cavities; and a force sensing element disposed within each of said plurality of cavities and operable to produce an output signal in response to flexing of said diaphragm, said force sensing element including four pairs of radially aligned strain gages, the strain gages of each pair arranged to measure differential strain in a radial direction and includes an inner gage mounted on said diaphragm adjacent the center of said circular diaphragm and an outer gage mounted on said diaphragm immediately adjacent said outer wall of said cylindrical cavity, wherein said circular diaphragm exhibits a micro-strain behavior under load that produces a maximum magnitude at a radial location from the center of said circular diaphragm, and further wherein said inner gage is positioned to span said maximum magnitude radial location.

4. In a telemetric knee prosthesis adapted to measure forces transmitted across the knee joint, the knee prosthesis having a femoral component, a tibial bearing member in articulating contact with the femoral component, a tibia engaging member and a tibial tray engaged to the tibial bearing member and the tibia engaging member, the tibial tray comprising:

an upper plate having a portion configured for engaging the tibial bearing member;

a lower plate having a portion configured for engaging the tibia engaging member, said lower plate spaced apart from said upper plate and defining a plurality of cylindrical cavities opening away from said upper plate, each of said plurality of cylindrical cavities including a circular diaphragm adapted to flex when subjected to a load normal to the diaphragm and an outer wall;

a plurality of support posts, each connected between said upper plate and said diaphragm of a corresponding one of said plurality of cylindrical cavities; and a force sensing element disposed within each of said plurality of cavities and operable to produce an output signal in response to flexing of said diaphragm, said force sensing element including four pairs of radially aligned strain gages, the strain gages of each pair arranged to measure differential strain in a radial direction and includes an inner gage mounted on said diaphragm adjacent the center of said circular diaphragm and an outer gage mounted on said diaphragm immediately adjacent said outer wall of said cylindrical cavity, wherein said circular diaphragm exhibits a micro-strain behavior under load that produces a zero-crossing point between the center of said circular diaphragm and said outer wall of said cylindrical cavity, and further wherein said outer gage is positioned between said zero-crossing point and said outer wall.

5. The tibial tray of claim 4, wherein said circular diaphragm exhibits a micro-strain behavior under load that produces a negative maximum magnitude at a radial location between said zero-crossing point and said outer wall, and further wherein said outer gage is positioned to span said negative maximum magnitude radial location.

6. The tibial tray of claim 4, wherein said circular diaphragm further exhibits a micro-strain behavior under load that produces a positive maximum magnitude at a radial location from the center of said circular diaphragm, and further wherein said inner gage is positioned to span said positive maximum magnitude radial location.

7. In a telemetric knee prosthesis adapted to measure forces transmitted across the knee joint, the knee prosthesis having a femoral component, a tibial bearing member in articulating contact with the femoral component, a tibia engaging member and a tibial tray engaged to the tibial bearing member and the tibia engaging member, the tibial tray comprising:

an upper plate having a portion configured for engaging the tibial bearing member;

a lower plate having a portion configured for engaging the tibia engaging member, said lower plate spaced apart from said upper plate and defining a plurality of cavities opening away from said upper plate, each of said plurality of cavities including a diaphragm adapted to flex when subjected to a load normal to the diaphragm, said lower plate further defining a central cavity disposed between said plurality of cavities and a plurality of wiring channels, each communicating between a corresponding one of said plurality of cavities and said central cavity;

a plurality of support posts, each connected between said upper plate and said diaphragm of a corresponding one of said plurality of cavities;

a force sensing element disposed within each of said plurality of cavities and operable to produce an output signal in response to flexing of said diaphragm said force sensing element including four pairs of radially aligned strain gages, the strain gages of each pair arranged to measure differential strain in a radial direction;

a circuit element disposed in said central cavity for processing said output signal from said force sensing element in each of said plurality of cavities; and wiring electrically connecting each force sensing element in said plurality of cavities to said circuit element to transmit said output signal, said wiring disposed in a corresponding one of said plurality of wiring channels, wherein said lower plate defines a plane perpendicular to the sagittal plane of the knee joint when the knee prosthesis is implanted therein, wherein each of said four pairs of strain gages is aligned in a one of two radial planes that are at about 45 degrees relative to said sagittal plane, and wherein none of said four pairs of radially aligned strain gages is aligned with said wiring channel communicating with said corresponding one of said plurality of cavities.

8. The tibial tray of claim 7, wherein said four pairs of radially aligned strain gages are aligned at an angle of about 45 degrees or 135 degrees relative to said wiring channel.

9. A telemetric knee prosthesis comprising:

an upper tibial tray plate having a portion configured for coupling with a tibial bearing member;

a lower tibial tray plate spaced apart from the upper tibial tray plate and defining a plurality of cavities opening away from the upper tibial tray plate, each of the plurality of cavities including an outer wall and a diaphragm adapted to flex when subjected to a load on the diaphragm;

a plurality of support posts, each of the plurality of support posts extending between the upper tibial tray plate and the diaphragm of a corresponding one of the plurality of cavities; and a plurality of force sensing elements, each of the plurality of force sensing elements disposed within one of the plurality of cavities and operable to produce an output signal in response to flexing of the diaphragm in the respective one of the plurality of cavities, each of the plurality of force sensing elements including an inner gage positioned such that at least a portion of the inner gauge is mounted at a location on one side of the diaphragm directly opposite to where a portion of the corresponding one of the plurality of support posts contacts the other side of the diaphragm.

10. The tibial tray of claim 9, wherein at least a portion of the inner gauge is mounted on the one side of the diaphragm at a radius of less than about 2.5 mm from the center of the diaphragm.

11. The tibial tray of claim 9, wherein the diaphragm is a circular diaphragm which exhibits a micro-strain behavior under load that produces a maximum magnitude at a radial location from the center of the circular diaphragm, and further wherein the inner gage is positioned to span the maximum magnitude radial location.

12. The tibial tray of claim 11, wherein:

the circular diaphragm exhibits a micro-strain behavior under load that produces a zero-crossing point between the center of the circular diaphragm and the outer wall of the cylindrical cavity; and each of the plurality of force sensing elements further comprises an outer gage positioned between the zero-crossing point and the outer wall.

13. The tibial tray of claim 9, wherein the support posts are circular in cross-section.

* * * * *